(12) United States Patent
Berggren et al.

(10) Patent No.: US 6,319,380 B1
(45) Date of Patent: Nov. 20, 2001

(54) USE OF AN EARLIER KNOWN SEPARATION MATERIAL AND NOVEL FORMS OF THE MATERIAL

(75) Inventors: Eva Berggren, Uppsala; Ilya Zelikman, Storvreta, both of (SE)

(73) Assignee: Amersham Pharmacia Biotech AB, Uppsala (SE)

( * ) Notice: Subject to any disclaimer, the term of this patent is extended or adjusted under 35 U.S.C. 154(b) by 0 days.

(21) Appl. No.: 09/101,944

(22) PCT Filed: Jan. 18, 1997

(86) PCT No.: PCT/SE97/00078

§ 371 Date: Mar. 11, 1999

§ 102(e) Date: Mar. 11, 1999

(87) PCT Pub. No.: WO97/26071

PCT Pub. Date: Jul. 24, 1997

(30) Foreign Application Priority Data

Jan. 18, 1996 (SE) .................................................. 9600171

(51) Int. Cl.[7] .......................... G01N 27/26; G01N 27/447

(52) U.S. Cl. .......................... 204/469; 204/456; 204/606; 536/51; 536/112; 526/238.2; 526/238.22

(58) Field of Search ...................................... 204/469, 456, 204/470, 466, 467, 606, 616, 617; 536/51, 112; 526/238.2, 238.22

(56) References Cited

U.S. PATENT DOCUMENTS 4,094,832 * 6/1978 Söderberg ........................ 526/238.22
4,314,897 * 2/1982 Monte et al. ..................... 204/616 X

OTHER PUBLICATIONS

Anthony T. Andrews, Electrophoresis Theory, Techniques and Bio–Chemical and Clinical Applications, 2nd edition, pp. 79, 100–102, 1986 (No month available).*

* cited by examiner

Primary Examiner—Jill Warden
Assistant Examiner—John S. Starsiak, Jr.
(74) Attorney, Agent, or Firm—Royal N. Ronning, Jr.

(57) ABSTRACT

The use of a gel produced by polymerization of a dextran derivative which exhibits groups that contain an alkene structure, for separating nucleic acid by electrophoresis.

16 Claims, No Drawings

USE OF AN EARLIER KNOWN SEPARATION MATERIAL AND NOVEL FORMS OF THE MATERIAL

FIELD OF THE INVENTION

The invention relates to the electrophoresis of single-stranded or double-strand nucleic acid (ss and ds respectively), primarily polynucleotides that consist of sequences of 5–20,000 nucleotides (alternatively base pairs).

It is known that gels based, inter alia, on agarose, polyacrylamides, bis-acrylamide, etc., can be used in the electrophoresis of nucleic acid.

The gels have normally been cast or molded in the presence of an electrophoresis buffer.

In the electrophoretic analysis of single-stranded DNA (sequencing) separation is normally effected in the presence of urea in order to keep the strands dissociated (Maniatis et al, Molecular Cloning: A Laboratory Manual, 2nd Ed., Cold Spring Harbor Laboratory Press (1989) New York, U.S.A.). Consequently, gels have been cast together with urea at a pH of about 8 in direct association with their use. Efforts to incorporate buffers of a higher pH value have also been made (Smith et al, Amer. Biotechnol. 8 (1990), 48–54). Problems Associated with Hitherto Known Techniques, and Desirable Properties of Relevant Gels Agarose gels that possess good sieving properties for the DNA-sequencing of samples are difficult to produce. Agarose also has the drawback that the gels readily become opaque and therefore are difficult to use in conjunction with optical detection. Drawbacks with polyacrylamide in electrophoresis is that the monomers (acrylamide and bisacrylamide) are toxic, and consequently great care must be observed when handling the monomers, and also that acrylates and acrylamides are hydrolysis sensitive. In the case of prefabricated gels that contain urea, the urea is also readily hydrolyzed.

As an alternative of subjecting single-stranded nucleic acid to electrophoresis in the presence of a denaturing agent, such as urea, electrophoresis may be carried out at an elevated pH (normally about pH 11) and/or at an elevated temperature (about 80–90° C.). Both alternatives result in the hydrolysis of polyacrylamide.

There is a strong general desire to find novel gel materials that can be used in the electrophoresis of nucleic acid. Objectives with regard to novel gel materials are that they shall:
1. Enable separation of single-stranded and/or double-stranded nucleic acid, primarily DNA, with a resolution that is comparable with or superior to commercial polyacrylamide gel (=PAA).
2. Enable the fabrication of gradient gels and gels that have different zones.
3. Provide low electro-endosmosis, preferably equal to or better than PAA.
4. Be stable in the pH range relevant to electrophoresis, normally 4–13.
5. Tolerate urea 8 M and other denaturing agents and conventional staining techniques for nucleic acid (e.g. silver staining and ethidium bromide staining).
6. Possess good optical properties, i.e. high light transmission 280–800 nm and non-disturbing (low) fluorescence, particularly at 480, 590 and 630 nm.
7. Be non-toxic.

The use of dextran derivative gels for protein electrophoresis was proposed about twenty years ago (Söderberg, L., U.S. Pat, No. 4,094,832). The gels were produced by free radical polymerization of a dextran derivative containing vinyl groups chosen from

and/or

where —A— is —$CH_2$— or —O— and R is H, $CH_3$, F, Cl, Br or CN. Polymerization could optionally be effected in the presence of low molecular vinyl compounds. Protein electrophoresis was the stated application. The advantages obtained were said to be that the gels were inert against biological substances, were stronger, could be cast with an incorporated electrophoresis buffer, could be cast or molded in the form of easily handled plates having tailor-made properties in accordance with the choice of vinyl substituents, charged substituents and copolymers, etc.

In conjunction with the attempt to produce electrophoresis gels that would give improved resolution of low molecular compounds, low "smiling", and improved optical properties, there have been proposed gels of polyhydroxy polymers cross-linked with a reagent that provides ether bridges with OH groups in the polymer (Kozulic, B., U.S. Pat. No. 5,371,208; see in particular column 11). The function of the gels has been shown for electrophoresis of DNA digested with the aid of restriction enzymes. Allyl agarose (Example 1) and dextran (Examples 14 and 16) can be mentioned from among a large number of examples.

A copolymer between acrylamide and allyl substituted agarose (Nochumsson, S., EP 87,995) has been proposed as a gel for electrophoresis, since such gels adhere well to conventional carrier or substrate materials.

OBJECT OF THE INVENTION

The object of the invention is to find novel gels for electrophoresis, which are suited for the separation of nucleic acid and which have improved properties with regard to the aforesaid objectives.

The invention

It has now been found that electrophoresis gels polymerized from a dextran derivative that includes groups having an alkene structure (>C=C<) are suited for electrophoretic separation of both single-stranded and double-stranded nucleic acids. The gels have improved properties with regard to several of the features mentioned in the aforegoing, such as chemical stability at high pH levels, optical clarity, are non-toxic and have a long shelf life. The polymer may be in the form of a copolymer with low molecular vinyl monomers. The gels concerned have earlier been defined in principle (Söderberg, L., U.S. Pat. No. 4,094,832).

The main aspect of the invention resides in a method for the gel electrophoretic separation of nucleic acid. The main feature of the method resides in the use of a gel which is a free radical-polymer of the same type as that used by S öderberg (U.S. Pat. No. 4,094,832). The method includes the steps typical in the gel electrophoresis of nucleic acid, i.e. the sample is placed on the gel and a voltage applied. When wishing to carry out electrophoresis on single-stranded DNA, the process is effected in the presence of a denaturing agent which dissociates double-stranded nucleic acid. See below. Alternatively, the electrophoresis can be carried out at elevated temperatures (e.g. temperatures above 50° C., a denaturing agent may be present when necessary).

Preferred groups that include alkene structures have the formula

where R may be H, F, Cl, Br or CN or a straight, branched or cyclic hydrocarbon group which may be saturated or unsaturated or contain an aromatic structure. Among saturated hydrocarbon groups, for instance groups according to the formula $C_nH_{2n+1}$ (n is an integer) can be mentioned those that contain ten or fewer carbon atoms (n integer $\leq 10$). The most preferred groups R are hydrogen (H) and lower alkyl groups having 1–4 carbon atoms, particular methyl ($CH_3$). The hydrogen atoms in $H_2C=$ may be substituted with halogen, particularly Cl or F. The hydrocarbon chain in a group R may be broken or one or more of the carbons may be substituted with one or more oxygen atoms in the same manner as the bridge B (see below).

The bridge B binds directly to an oxygen atom in a hydroxyl group of dextran. The bridge B is a straight, branched or cyclic hydrocarbon bridge which may be saturated or unsaturated and is optionally broken by ether oxygen and/or has one or more carbon atoms that are substituted with one alcoholic hydroxyl group. The bridge B may include aromatic structures, such as phenylene (as cyclic structures; —$C_6H_4$—). The bridge B may alternatively be a single bond. At most, one oxygen atom is directly bound to one and the same carbon atom. The length of the bridge is normally less than 1–15 atoms, including any oxygen atoms. Unsubstituted hydrocarbon bridges are for instance —$(CH_2)_n$—, where n is an integer chosen from 1–10, for instance 2, 3 or 4. Phenylene, cyclohexandiyl, etc., are examples of cyclic structures that can be included in the bridge.

Specific examples of the group $H_2C=CR$—B— allyl, 3-allyloxy-2-hydroxy-propyl, 3-(styryl-4-oxy)-2-hydroxypropyl, 1-methylallyl, 1-chloro-allyl and non-substituted vinyl, etc. See Söderberg, L. (U.S. Pat. No. 4,094,832) for further examples.

The substitution degree of the dextran derivative with respect to alkene-containing groups is suitably 0.05–1.9, preferably 0.5–1.2, mmol/g dry dextran derivative (=1–30% and 5–25% respectively).

The molecular weight of the dextran derivative may vary within wide limits. Starting from non-substituted dextran, the mean molecular weight (Mw) will preferably lie in the range of 10,000–10,000,000 Da, particularly 70,000–5,000,000 Da.

By suitable combinations of polymerization conditions (substitution degree, initiator, dextran concentration, the molecular weight of dextran, etc.) gels that have different properties can be produced for the electrophoresis of nucleic acid.

The dextran derivative is produced in a known manner (see, for instance, Söderberg, L., U.S. Pat. No. 4,094,832).

The low molecular vinyl compound (normally a monovinyl compound or divinyl compound) with which copolymerization may be carried out may be an acrylamide or a methacrylamide which may be substituted at the nitrogen atom or at one of the double-bonded carbon atoms. Alternatively, there may be used other low molecular vinyl compounds that have equivalent stability properties against hydrolysis in the relevant pH ranges and temperature ranges. The vinyl compound will preferably contain at most twenty carbon atoms, preferably at most ten carbon atoms. C.F. Söderberg, L., U.S. Pat. No. 4,094,932.

The polymerization conditions are those typical for the polymerization of alkene groups (electron-radiation or γ-radiation, oxidative radical polymerization, etc.), preferably free radical polymerization being chosen in this regard. UV-initiators of, e.g., a benzophenone or a benzoyl derivative, and chemical initiators such as persulphates, peroxides and azobisisonitrile can be used. Accelerators are used when necessary. The quantity of dextran derivative used normally corresponds to 20–100% (w/w) calculated on the total amount of polymerizable reactants.

Dextran gels can be cast with a buffer system incorporated in the polymerization solution. For instance, there can be produced prefabricated gels which include buffer components that provide a pH within the relevant pH range, e.g. pH 7–10 or 10–13. The buffering components will normally have pKa values within the relevant ranges. In accordance with the aforegoing, denaturing agents that dissociate double-stranded nucleic acid, primarily urea and formamide may be incorporated in respect of the lower range. See Levine et al, Biochemistry 2(1) (1963), 168–175 (which is herewith incorporated in the present document by reference). With regard to the upper range, suitable buffer components are bases that are stronger than ammonia, for instance borates, soluble hydroxides ($OH^-$), carbonates ($CO_3^{2-}$), phosphates ($PO_4^{3-}$) and certain primary and secondary amines, of which 2-amino-2-methyl-1-propanol can be mentioned among others. The buffer components will preferably not be volatile, implying that their boiling points will normally be above 120° C. Typical electrophoresis buffer systems are described in U.S. Pat. No. 5,055,517 (column 15–16) (which is herewith incorporated by reference).

The gels can be cast so as to contain different zones, e.g. a less dense stacking zone and a denser separation zone. The gels may also be cast as gradient gels and in different geometries, such as in rectangular cassettes, in channels of different cross-sectional shapes, including capillaries.

Gels of the type concerned are often relatively weak from a mechanical aspect. When the gels are to be treated as a "slab" gel, the gels will preferably be cast on a carrier or substrate in a known manner, normally a polymer film (e.g. GelBond® PAG (FMC, USA)).

According to one particular aspect of the invention, an electrophoresis gel is fabricated from a dextran derivative polymer in accordance with the aforegoing. This aspect of the invention is characterized in that the gel includes buffer components and denaturing agents according to the aforegoing.

For further information relating to conditions for polymerization and the production of dextran derivatives, the reader is referred to the aforementioned patent publications (incorporated by reference) and also to textbooks on the subject.

EXPERIMENTAL SECTION

Preparation of Allyl Dextran Solutions

Allyl dextran solutions (Mw 2,000,000 g/mol, allyl content of 1.2–1.5 mmol/g dry substance ($CH_2=CH-CH_2$— being substituted at an OH of dextran), were prepared by dissolving a given quantity of allyl dextran in a volume of buffer (TRIS-HCl 0.375 M pH 8.8), which was slightly less than desired. This is because the volume of the buffer increases when dextran dissolves. After all allyl dextran had dissolved, the volume was adjusted to the desired volume with buffer. Urea was added in certain instances.

Example I

Electrophoresis of Single-Stranded Nucleic Acid

Gel Casting and Processing

A. Gel Containing Urea, pH about 8.2

A solution containing 14% w/v allyl dextran in TRIS-HCl (0.375 M, pH 8.8) and urea (7 M) was prepared. 250 µl ammonium persulphate solution (0.1 g/ml in TRIS-HCl 0.375, pH 8.8) was stirred into 50 ml of the solution of allyldextran. The solution was de-aerated for about 3–5 minutes with the aid of a vacuum pump. 25 µl of an accelerator (TEMED=N,N,N',N'-tetramethylethylenediamine) while carefully stirring so as to avoid contamination with air. The mixture was allowed to stand for roughly 5 minutes, until all air bubbles had disappeared. The solution was then sucked into a syringe (30ml) and a cassette (short 15 cm) for ALFexpress DNA Sequencer (Pharmacia Biotech AB, Uppsala, Sweden) was filled with a gel by capillary suction of the solution. It took roughly 5 minutes to fill the cassette and roughly 30–45 minutes to polymerize the solution, counting from the time at which TEMED was added.

The gel was evaluated electrophoretically in an ALFexpress DNA Sequencer, by separating single-stranded DNA (ssDNA). The samples separated were fragment samples comprising a 50-base pair ladder 50–500 bp and a sequence sample M13. Both samples were labelled or marked with Cy-5 and had been obtained from Pharmacia Biotech AB, Reagents Division (Milwaukee, U.S.A.). The samples were prepared in accordance with standard methods for processing on ALFexpress with polyacrylamide gel. The tank buffer was TRIS-borate-EDTA (0.1M, 0.08 M, 1 mM, pH 8.2). The gel was processed with the following parameters: U=1000 V, I=60 mA, P=15 W, T=55° C. The effect was limiting. The gel was pre-processed with these parameters for 50 minutes prior to adding the samples.

B. Gel Without Urea, pH about 11

A solution containing 13% w/v allyl dextran in 2-amino-2-methyl-1-propanol (100 mM, pH 11.2) was prepared. 500 µl of an ammonium persulphate solution (0.1 g/ml in solution of 2-amino-2-methyl-1-propanol (100 mM) was stirred into 50 ml of the solution of allyl dextran. The solution was de-aerated with the aid of a vacuum pump over a period of about 3–5 minutes. 50 µl TEMED were then added, while carefully stirring the system. The solution was then treated in the same manner as in the preceding experiment prior to casting the gel in a cassette (short 15 cm) for an ALFexpress DNA Sequencer.

The gel was evaluated with the same samples and in the same way as in the preceding experiment. The tank buffer was 100 mM 2-amino-2-methyl-1-propanol, pH 11.2.

Results and Discussions

Gel Casting for ALFexpress DNA Sequencer

The initiator system ammonium persulphate-TEMED functioned well for allyl dextran. The time taken to fill a gel cassette with reaction solution was slightly longer than in the case of a conventional acrylamide solution. It was possible to adapt the induction time so as to enable the solution to be de-aerated and the gel cassette filled prior to commencement of the polymerization process. On a molar basis, the amount of initiator used when urea was present was the same as the amounts normally used for the preparation of acrylamide-urea gels for ALFexpress DNA Sequencers. The double amounts of the initiator and accelerator were required to obtain polymerization within the same time frames without urea but with 2-amino-2-methyl-1-propanol in the buffer. This is probably because polymerization is inhibited at a high pH and when amines are present, therewith requiring higher concentrations of initiator plus accelerator in order to start polymerization.

Optical Quality

The gels that had been cast with the initiator system ammonium persulphate plus TEMED exhibited sufficiently good optical clarity to enable laser-induced florescence to be used for detection purposes (e.g. ALFexpress DNA Sequencer). The solutions from which the first gels were cast were not de-aerated prior to casting. This resulted in tendency towards less clear gels. It is probable that small air bubbles cause the light to be spread and therewith result in less clear gels, which in turn makes laser detection more difficult to achieve.

Electrophoresis, Gel Containing Urea, pH 8.2

The system was pre-run for 50 minutes, since the selected buffer system was discontinuous (TRIS-HCl in the gel and TRIS-borate-EDTA in the tank). Without pre-running, there is a danger that low molecular fragments will stack behind the chloride-ion front. In the case of the fragment containing sample, the primer peak arrives after about 20 minutes, followed by the ten fragments. Separation was of the same quality as that achieved with polyacrylamide gel. Up to about 240 bases were separated for the sequence sample. The peaks then became wider and it was impossible to read a sequence. Of the 200 first bases, 16 were wrong. The faults, with the exception of one, were all deletions, i.e. where there should have been one or more of the same bases in sequence one less base was identified, for instance one of two or three of four. This deviation may have been because the algorithm used was not adapted to the gel. The tests showed that it is possible to separate ssDNA on an allyl dextran gel that is polymerized with the system ammonium persulphate plus TEMED, and that detection can be effected with laser-induced fluorescence.

Electrophoresis, Gel in the Absence of Urea, pH 11.2

The gel was run with a continuous system using the same buffer in tank and gel. In the case of the fragment sample, the primer peak arrived after little more than 20 minutes. The first fragment (50 and 100 bp) gave no distinct peaks (rounded). No explanation could be found for this. On the other hand, the subsequent fragments (150–500 bp) were very distinct and separation appeared normal. The total separation time was roughly the same as that for corresponding allyl dextran gel including urea (pH 8.2). No sequencing could be obtained in the case of the sequence sample (M13). The primer peaks could be seen, but then no more than noise. The experiment was repeated, but with the same result. According to information from the sample supplier, the fluorophore in the labelled sample had limited stability at high pH values and for certain amines. This may be one explanation for the "no result" result for the sequence sample. Marking or labelling of the primer and of the fragment sample was much stronger, which may be the reason why these could be shown. The obtained results show that gel containing no urea and having a high pH is able to separate single stranded fragment samples with approximately the same resolution as for a gel that contains urea and has a lower pH. More study is required to establish why the sequence sample could not be seen.

Example II

Electrophoresis of Double-Stranded Nucleic Acid

Gel Casting and Processing

120 µl of ammonium persulphate solution (0.1 g/ml in TRIS-HCl 0.375, pH 8.8) were stirred into a solution of 17% w/v allyl dextran in TRIS-HCl (0.375, pH 8.8). The solution was deaerated for about 5 minutes with the aid of a vacuum pump. 15 μl TEMED=N,N,N',N'-tetramethylethylenediamine were then carefully stirred into the solution. The solution was allowed to stand for about 5 minutes until all air bubbles had disappeared. The solution was then sucked into a syringe and delivered to a gel cassette consisting of a glass plate and an aluminium oxide plate. The gel had a size of 8.5×9 cm. A film (GelBond®, FMC, USA) of the same size lay against the aluminium oxide sheet. The film functioned as a carrier, because the allyl dextran gels were too weak mechanically to be handled on their own. The gel was cast in the absence of stack zones and with combs to create sharply defined wells for sample deposition. The polymerization process commenced about 45 minutes after adding TEMED. The gel was allowed to stand for one hour before being processed.

The gel was evaluated in Mighty Small SE 260 (Hoefer Scientific Instruments, California, U.S.A.) with the fragment samples Hinc and Hae (Hinc II DIGEST FX-174-RF (13 fragments from 1057–79 base pairs) and Hae III DIGEST FX-174-RF (11 fragments from 1353 to 72 base pairs) (Pharmacia Biotech AB, Uppsala, Sweden). The tank buffer used was TRIS-glycine (0.025 M, 0.192 M, pH 8.3). The gel was run for about 12 minutes with I=15 mA prior to charging the samples. The voltage varied during this period from 60 V to 110 V. The samples were then delivered to the gel and separation was effected with I=25 mA. The gel was processed to the front with bromo-phenol blue was about 2 cm from the gel edge. This took about 50 minutes and the voltage changed from 190 V to 400 V and the power from 5 W to 10 W. The gel was developed by silver staining. The time for developing the gel was about 30 minutes longer than the time for developping a polyacrylamide gel. The surface of the gel became "crackled" in the fixing bath (solution containing 10% acetic acid) in the development process. This may be due to surface contraction of the gel. This crackling made it difficult to interpret the obtained bands. All bands were not included, although the separation of dsDNA fragments was distinct.

Example III

Gel Preparation with the Aid of an UV-initiator

Gels were produced in separate tests with the aid of an UV-initiator (Irgacure® 184 (1-hydroxy-cyclohexyl phenyl ketone) molecular weight 204, Ciba-Geigy) and the same allyl dextran derivative as that defined above. Preparation was found to be sensitive, due to the solubility properties of the initiator. The gels obtained by this method were fully in class with those obtained by chemical initiation (ammonium persulphate plus TEMED).

Summary: Other Properties of the Synthesized Gels

No disturbing electroendosmosis could be observed with the gels. Turbidity has, as a rule, been comparable with that obtained with conventional polyacrylamide gels. The intrinsic fluorescence values measured at 630 nm showed that background fluorescence was acceptable. Backgrounds of 3% were measured at 630 nm, which is slightly higher than the values obtained with polyacrylamide gels. This is in no way disturbing, however. Adhesion with regard to relevant carrier materials was good. With regard to GelBond Pag, the gel adhered both to the hydrophilic and the hydrophobic side. The finished gel remained seated during treatment with those solutions applicable for silver staining. The mechanical properties of the gels render them weaker than polyacrylamide gels. They are readily torn if handled in the absence of a carrier substrate. No problem with regard to swelling of the gels was encountered during the electrophoresis.

Experimental Support Obtained During the Priority Year

During the priority year Swedish patent application 9600612-7 has been filed. It deals with polyhydroxy polymers carrying styryl ether groups. SE 9600612-7 is hereby incorporated by reference.

The application gives the manufacture of styryl glycidyl ether by first synthesizing 4-(2,3-epoxypropoxy) benzaldehyde from 4-hydroxy benzaldehyde and epichlorohydrin in the presence of NaOH, tetra-n-butyl ammonium iodide and dimethylsulfoxide. 4-(2,3-epoxypropoxy) benzaldehyde was then added to a dry tetrahydrofuran solution (0° C., argon atmosphere) containing suspended methyl-triphosphonium bromide, catalytic amounts of 18-crown-6-ether and potassium t-butoxide. From this mixture styryl glycidyl ether was then obtained in a yield of 70%.

Styryl glycidyl ether was then reacted in various ways with dextran (Mw 40,000 Da or 500,000 Da). Various ratios styryl glycidyl ether to dextran, various solvents (pure water, pure DMSO), various mixtures of solvents (water, DMSO, toluene), various amounts of bases (NaOH and where appropriate sodium dimsyl) and in some instances also a phase transfer catalyst were used. Degrees of substitution ranging from 0 up to 50% were accomplished.

A styryl ether dextran so obtained (degree of substitution 2.8%) dissolved to a concentration of 15% (w/v) in urea (7M) containing Tris-HCl buffer (0.375 M, pH 8.8) was polymerized to a gel with a radical initiator. The utility of the gel was then illustrated by subjecting a sample containing double-stranded DNA to electrophoresis on the gel.

What is claimed is:

1. In a method for separating nucleic acids by the electrophoresis, wherein a gel is utilized as an electrophoresis medium and an electric field is applied across the surface of the gel to separate the nucleic acids, the improvement comprising using, as the gel, a gel prepared by polymerization of a dextran derivative having groups that contain an alkene structure.

2. The method according to claim 1, wherein said groups have the structure

where

R is H, hydrocarbon group, F, Cl, Br or CN, and the free valance binds to an hydroxylic oxygen in dextran, and B is a straight, branched or cyclic hydrocarbon bridge which is optionally broken by ether oxygen and/or substituted with one or more alcoholic hydroxyl groups.

3. The method according to claim 2, wherein R is hydrogen.

4. The method according to claim 2, wherein B is —CH$_2$— or —CH$_2$—O—CH$_2$—CH(OH)—CH$_2$—.

5. The method according to claim 2, wherein R is CH$_3$.

6. The method according to claim 1, wherein the nucleic acid is DNA.

7. The method according to claim 1, wherein the nucleic acid is single-stranded.

8. The method according to claim 1, wherein the nucleic acid is double-stranded.

9. The method according to claim 1, wherein the nucleic acid has less than 20,000 bases if single-stranded or less than 20,000 base pairs if double-stranded.

10. The method according to claim 9, wherein electrophoresis is carried out at a temperature at which the nucleic acid exists in single-stranded form, preferably >50° C. or in the presence of a denaturing agent which causes the nucleic acid to exist in single-stranded form at pH 7–10 or at elevated pH 10–13.

11. The method according to claim 1, wherein said gel is produced by polymerization of a dextran derivative exhibiting groups having an alkene structure, and wherein said gel includes a stacking zone of less dense gel structure and a separation zone of denser gel structure.

12. The method according to claim 1, wherein said gel is produced by polymerization of a dextran derivative exhibiting groups having an alkene structure, and wherein said gel is carried by a supporting plastic material.

13. The method according to claim 12, wherein said supporting plastic material is an intermediate film that enhances adhesiveness and stability.

14. The method according to claim 1, wherein said gel is produced by polymerization of a dextran derivative exhibiting groups having an alkene structure, and wherein said gel is cast in channels or in rectangular moulds.

15. A gel produced by polymerization of a dextran derivative exhibiting groups having an alkene structure comprising:

$$H_2C=CR-B-$$

where
- R is H, a hydrocarbon group, F, Cl, Br or CN, and
- the free valance binds to an hydroxylic oxygen in dextran, and
- B is a straight, branched or cyclic hydrocarbon bridge which is optionally broken by ether oxygen and/or substituted with one or more alcoholic hydroxyl groups said gel being hydrated with a buffer giving a pH value in the range of 10–13.

16. A gel produced by polymerization of a dextran derivative exhibiting groups having an alkene structure comprising:

$$H_2C=CR-B-$$

where
- R is H, a hydrocarbon group, F, Cl, Br or CN, and
- the free valance binds to an hydroxylic oxygen in dextran, and
- B is a straight, branched or cyclic hydrocarbon bridge which is optionally broken by ether oxygen and/or substituted with one or more alcoholic hydroxyl groups said gel being hydrated with a buffer set to a pH value in the range of 7–10 and containing a denaturing agent which dissociates double-stranded nucleic acid.

* * * * *